United States Patent [19]
Lam

[11] Patent Number: 5,953,018
[45] Date of Patent: Sep. 14, 1999

[54] POST PROCESSING METHOD AND APPARATUS FOR REVERSIBLY CONVERTING AN ERASE BAR ECG WAVEFORM DISPLAY TO A SCROLLING ECG WAVEFORM DISPLAY

[75] Inventor: Siu Lam, Woodcliff Lake, N.J.

[73] Assignee: Datascope Investment Corp., Montvale, N.J.

[21] Appl. No.: 08/969,408

[22] Filed: Nov. 7, 1997

[51] Int. Cl.$^6$ ........................................... G06F 15/00
[52] U.S. Cl. ................................................. 345/440
[58] Field of Search ........................ 345/440, 441, 345/442, 115, 116, 134, 135

[56] References Cited

U.S. PATENT DOCUMENTS

| | | | |
|---|---|---|---|
| 4,873,514 | 10/1989 | Nakagawa | 340/726 |
| 5,289,575 | 2/1994 | Godfrey | 395/162 |
| 5,684,508 | 11/1997 | Brilman | 345/134 |

*Primary Examiner*—Phu K. Nguyen
*Attorney, Agent, or Firm*—Abraham P. Ronai

[57] ABSTRACT

An apparatus and post-processing method for reversibly converting an existing electrocardiograph (ECG) erase bar waveform display to a scrolling waveform display. This conversion is accomplished by swapping the positions of the portions of the waveform that are displayed to the right and left of the erase bar in an erase bar waveform display each time a new heartbeat data point is displayed. The swapping function is accomplished by delaying the display of the data points to the right of the erase bar by a time period x and by delaying the display of data points to the left of the erase by x plus the amount of time required to scan an entire row. x is the amount of time required to scan all of the data points displayed to the right of the erase bar on the erase bar waveform display.

10 Claims, 4 Drawing Sheets

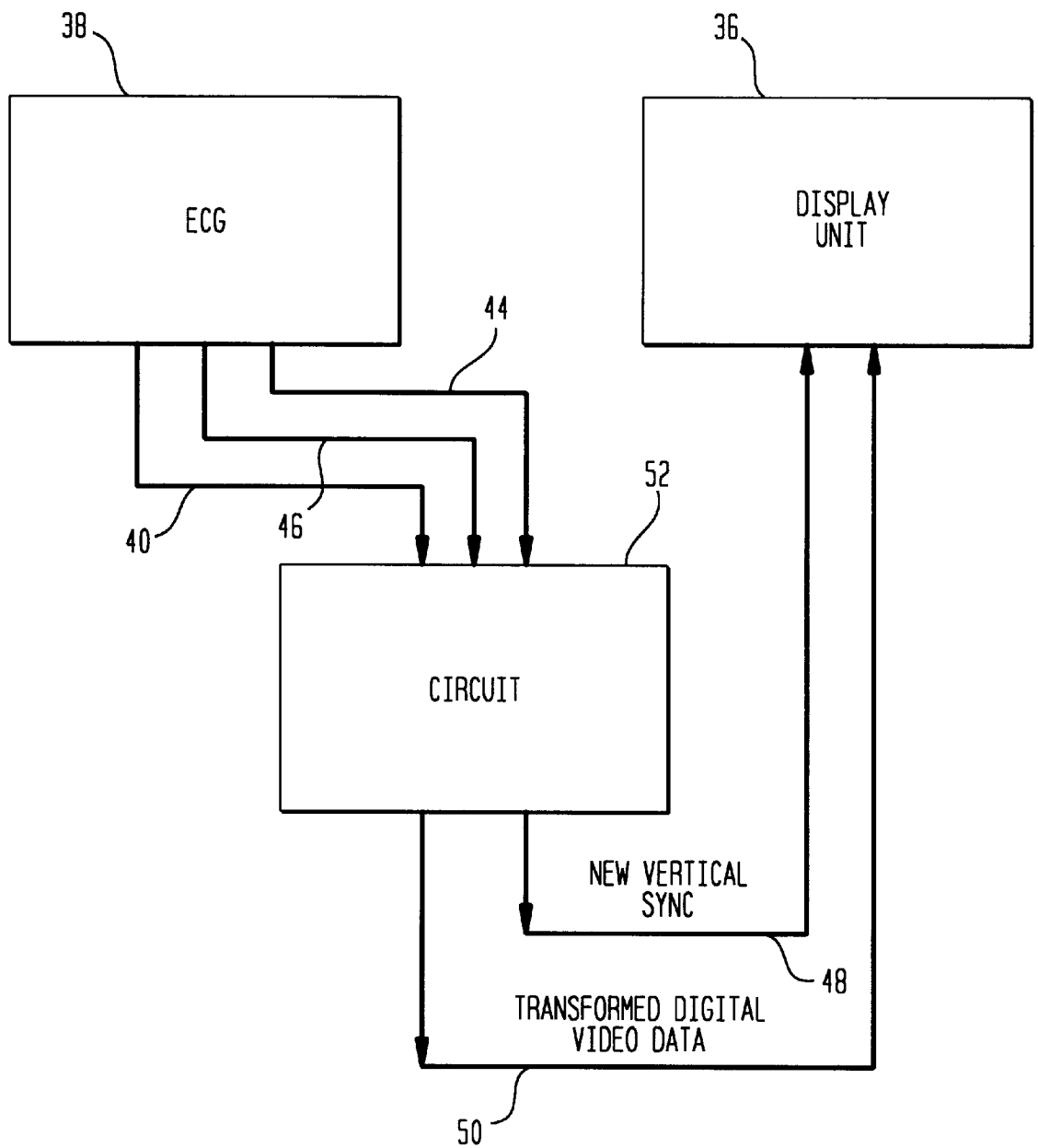

POST PROCESSING METHOD AND APPARATUS FOR REVERSIBLY CONVERTING AN ERASE BAR ECG WAVEFORM DISPLAY TO A SCROLLING ECG WAVEFORM DISPLAY

BACKGROUND OF THE INVENTION

1. Field of the Invention

The invention relates to a post processing method and apparatus for generating a scrolling waveform display from an existing erase bar waveform display. More particularly, the invention relates to a device and post processing method for reversibly converting an electrocardiograph system (ECG) with an existing erase bar waveform display to one with a scrolling waveform display.

2. Description of the Prior Art

Doctors often have to make critical split second decisions while treating patients. To facilitate the clinical decision making process hospitals and clinics are equipped with a myriad of biomedical devices. One such device is the ubiquitous ECG. The ECG monitors and displays a patient's vital signs. Although the information that the ECG provides is extremely valuable many clinicians have indicated a dissatisfaction with the manner in which this information is displayed by the ECG display unit and thereby communicated to them.

The current ECG display procedure, with which many clinicians are dissatisfied, involves an "erase bar." As soon as the ECG is turned on the display unit screen displays a waveform (each pulse representing a heartbeat) which begins on the left most side of the display unit screen and proceeds towards the right side of the display unit screen. Once the waveform reaches the right most side of the display unit screen (such that the waveform extends from the right most side of screen to the left most side of the screen) an erase bar, moving from left to right and starting on the left most side of the screen, begins to erase the waveform. The erase bar typically has a leading edge facing the right side of the display unit screen and a trailing edge facing the left hand side of the screen. As the oldest data points of the first waveform are being erased on the leading edge of the erase bar, new data points are displayed on the trailing edge of the erase bar thus forming a new waveform.

Use of the erase bar display method for displaying ECG waveforms has two main drawbacks. First, the erase bar method forces the user to follow the trailing edge of the erase bar in order to see how the waveform is changing. If a clinician wants to read the ECG output waveform he or she must spend precious time: (1)first locating the erase bar on the display unit screen; and (2)then shifting his or her eyes to the left of the erase bar (the trailing edge) to see the new waveform being displayed. The second main drawback of the erase bar display method relates to individual heartbeat comparisons. In order to compare the two most recent individual heart beat pulses using the erase bar display method a clinician must: (1)isolate the erase bar on the display unit screen; (2)look to the left of the erase bar (the trailing edge) and locate the most recent pulse; and (3)compare this pulse to the second most recent pulse, which could be at the right most side of the display unit screen (since the erase bar moves across the screen). This process is not only time consuming but is also error prone. This is especially so if several waveforms are displayed simultaneously, each moving at different rates, forcing the erase bars to be unsynchronized (displayed in different locations).

A scrolling waveform display method eliminates the above mentioned drawbacks of the erase bar display method. In a scrolling waveform display the most current waveform information is fixed at one location (usually the right most portion of the display unit screen). The waveform flows from right to left without the presence of a distracting erase bar. The entire continuous waveform scrolls to the left, erasing the oldest data point on the left most portion of the display unit screen on a frame-by-frame basis, and allowing the newest data point to be drawn on the right most portion of the display unit screen. In order to compare the two most recent heartbeat pulses one simply has to recognize that the waveform is continuous and that all of the heartbeat pulses are ordered time wise. The earliest heartbeat pulse is displayed furthest left on the display unit screen and the most recent heartbeat pulse is displayed furthest right on the display unit screen.

Several methods have been used to generate a scrolling waveform display in the past. One such method, involves hardware that shifts memory address locations. For example, consider a memory unit that has four memory locations: location 1, location 2, location 3, and location 4. Data in each memory location indicates whether a certain pixel on the ECG display screen should be on or off (assuming a black and white display). Assume that the screen only has four pixels: pixel 1, pixel 2, pixel 3, and pixel 4. Data in location 1 controls pixel 1. Similarly, data in locations 2,3, and 4 control pixels 2,3, and 4, respectively. Data is first stored in each memory location. Next, the data is displayed on the ECG screen. In order to create a scrolling effect, before a new data point can be stored in memory, the data in location two must be shifted to location one and the data in location 3 must be shifted to location 3. Once this shifting is completed, the new data can be store in location 4. Now that the memory has been refreshed with the updated data, the data can be displayed on the screen. Since the newest data is always stored in location 4, which controls pixel 4, the newest data point will always appear on the right most side of the display screen, thus creating a scrolling waveform.

U.S. Pat. No. 5,289,575, by Nakagawa and Nojima, discloses a video display system for vertically scrolling text in selected portions of a display. The video display system disclosed employs the memory address shifting method discussed above to create scrolling.

A disadvantage with the above mentioned method involves variable scroll rates. Specialized display hardware can be designed to accomplish memory address shifting, however, as a result of the design of the hardware required to produce scrolling (shifting data in memory locations) there can only be one scroll rate. If there are three different waveforms being displayed on the display screen they must all scroll at the same rates. Furthermore, the entire screen must scroll. This is a problem for an ECG display unit where it is desired that only the waveforms scroll and not the vital sign numbers. The reason that there is only one scroll rate is because the data displayed on the display screen all comes from a single memory unit, which can only have one shift rate (rate of shifting data between adjacent memory locations).

High end scrolling waveform displays overcome this problem by having more than one memory unit. Waveforms are made to scroll at different rates by changing the shift rates of each individual memory unit. This technique is widely used in computer type applications. U.S. Pat. No. 4,873,514, for example, by Godfrey, discloses a hardware system having two memory units so as to allow for a single portion of the display to scroll while the rest of the display remains stationary. A disadvantage of this solution, however, is that it requires specialized and costly hardware: multiple memory units, commonly referred to as video planes (one for each simultaneous scrolling speed, including the static background).

A second method used to generate a scrolling waveform involves real time animation software. Such software basically redraws the entire waveform on a frame by frame basis. Every time a new data point is collected the data displayed by each pixel must be recalculated and restored. Implementing this method, therefore, requires a great deal of extra processing, and as a result, is very expensive.

While these methods may be suitable for the particular purpose employed, or for general use, they would not be as suitable for the purposes of the present invention as disclosed hereafter.

SUMMARY OF THE INVENTION

Accordingly, it is an object of the invention to provide a novel post processing method and apparatus for converting an electrocardiograph system (ECG) with an existing erase bar waveform display to one with a scrolling waveform display.

It is another object of the invention to provide a less costly scrolling waveform display unit.

It is a further object of the invention to provide an ECG system, with an existing erase bar waveform display format, which can be reversibly converted to an ECG system with a scrolling waveform display.

It is a still further object of the invention to provide an ECG system with a variable speed scrolling waveform display.

The invention is an apparatus and post-processing method for reversibly converting an existing electrocardiograph (ECG) erase bar waveform display to a scrolling waveform display. This conversion is accomplished by swapping the positions of the portions of the waveform that are displayed to the right and left of the erase bar in an erase bar waveform display each time a new heartbeat data point is displayed. The swapping function is accomplished by delaying the display of the data points to the right of the erase bar by a time period x and by delaying the display of data points to the left of the erase by x plus the amount of time required to scan an entire row. x is the amount of time required to scan all of the data points displayed to the right of the erase bar on the erase bar waveform display.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 2A is a block diagram consisting of a circuit connected between an ECG and a waveform display unit.

DETAILED DESCRIPTION OF THE PREFERRED EMBODIMENTS

Figure 1C:
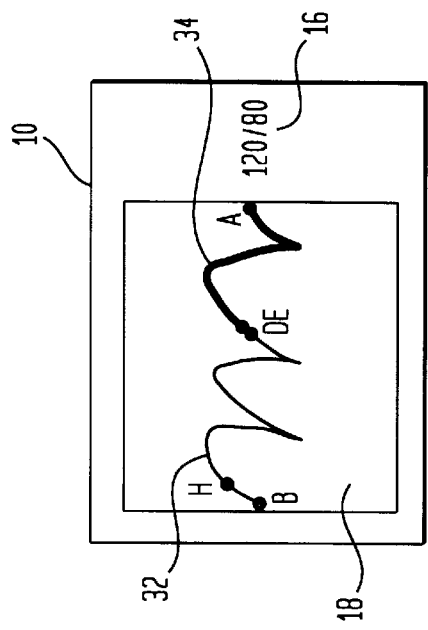
FIG. 1C is a front view of the same ECG display unit illustrated in FIG. 1A after the waveform portions on both sides of the erase bar have been swapped positions.
Figure 1D:
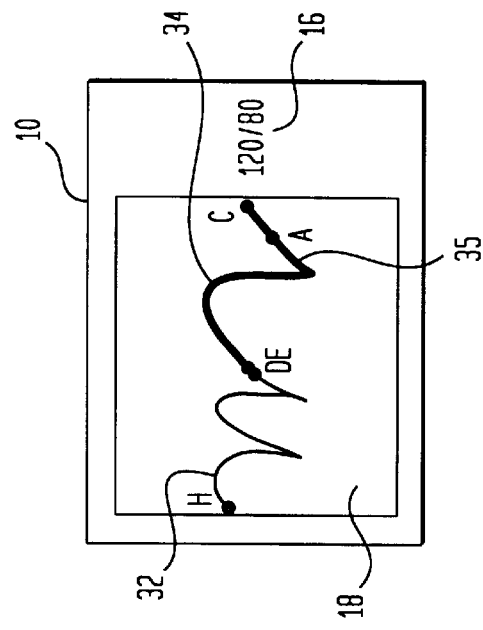
FIG. 1D is a front view of the same ECG display unit illustrated in FIG. 1B after the waveform portions on both sides of the erase bar have swapped positions.
Figure 1A:
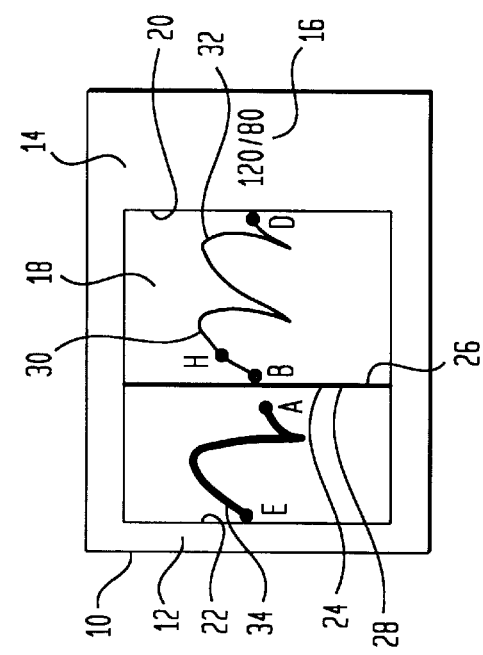
FIG. 1A is a front view of an ECG display unit with an erase bar waveform display.
Figure 1B:
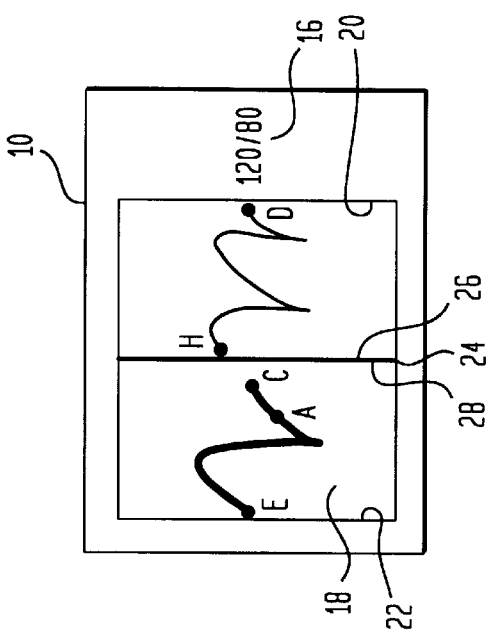
FIG. 1B is a front view of the same ECG display unit illustrated in FIG. 1A after updating the display with the most recent heartbeat data point.

FIGS. 1A and 1B illustrate an ECG display unit 10 with an erase bar waveform display format. FIG. 1A illustrates a front view, at time T1, of an ECG display unit 10 having a display unit screen 12. The display unit screen 12 has a waveform display portion 18 and a stationary background 14. Displayed on the stationary background 14 are vital sign numbers 16. The waveform display portion 18 has a right side 20, a left side 22, and an erase bar 24. Said erase bar 24 has a leading edge 26 and a trailing edge 28. Heartbeat pulses 30 (representing a person's heartbeat over the period of the heartbeat pulse 30) are displayed to the right and left of the erase bar 24. The heartbeat pulses 30 to the right of the erase bar form a post-erase bar waveform 32. The heartbeat pulses to the left of the erase bar 24 form a pre-erase bar waveform 34. For illustration purposes only, the pre-erase bar waveform 34 is be bolded so as to be able to clearly distinguish between the pre-erase bar waveform 34 and the post-erase bar waveform 32. Point A on the pre-erase bar waveform 34, monitored at time T1, represents the most recent patient heartbeat data point. Point B on the post-erase bar waveform 32 represents the oldest heartbeat data point. Point D on the post-erase bar waveform 32 represents the right most point on the waveform display portion 18. Point E on the pre-erase bar waveform 34 represents the left most point on the waveform display portion 18.

As soon as the ECG display unit 10 is turned on, the waveform display portion 18 displays a waveform which begins on the left side 22 of the waveform display portion 18 and proceeds towards the right side 20 of the waveform display portion 18. As soon as the waveform extends from the left side 22 of the waveform display portion 18 to the right side 20 of the waveform display portion 18, the erase bar 24, moving from left to right and starting on the left side 22 of the waveform display portion 18, begins to erase the waveform. As soon as the erase bar 24 appears on the left side 22 of the display unit screen 12 the portion of the waveform to the right of the erase bar 24 becomes the post-erase bar waveform 32. Furthermore, as the oldest heartbeat data points of the waveform are being erased at the leading edge 26 of the erase bar 24, new heartbeat data points are displayed on the trailing edge of the erase bar and thus form the pre-erase bar waveform 34.

FIG. 1B illustrates the display unit 10, illustrated in FIG. 1A, at time T1+Thb (after another heartbeat data point has been collected), where Thb is the heartbeat sampling period. As can be seen in FIG. 1B, the erase bar 24 has moved towards the right side 20 of the waveform display portion 18. Point B is not seen in FIG. 1B because it has been deleted at the leading edge 26 of the erase bar 24. Point A has remained in the same position but is no longer the most recent heartbeat data point. Point C now represents the most recent heartbeat data point and Point A now represents the second most recent heartbeat data point. The erase bar 24 will continue to move towards the right side 20 of the waveform display portion 18 until the pre-erase bar waveform 34 extends from the left side 22 of the waveform display portion 18 to the right side 20 of the waveform display portion 18. Once the erase bar 24 reaches the right side 20 of the waveform display portion 18, and has erased every heartbeat data point in its path, it will appear once again on the left side 20 of the waveform display portion 18 and the entire process will repeat.

FIGS. 1C and 1D illustrate how swapping the positions of the post-erase bar waveform 32 and the pre-erase bar waveform 34, as illustrated in FIGS. 1A and 1B, each time a heartbeat data point is displayed, creates a scrolling effect.

FIG. 1C illustrates a snap shot of the display unit 36 at time T1 with the post-erase bar waveform 32 and the pre-erase bar waveform 34 having swapped position. The post-erase bar waveform 32 formerly located to the right of the pre-erase bar waveform 34 (as illustrated in FIG. 1A) is shifted to the left of the pre-erase bar waveform 34 such that point E on the pre-erase bar waveform 34 is displayed just one pixel column to the right of Point D on the post-erase bar waveform 32.

FIG. 1D illustrates a snapshot of the display unit 36, at time T1+Thb, with the post-erase bar waveform 32 and the pre-erase bar waveform 34 having swapped positions. Here too, the post-erase bar waveform 32 formerly located to the right of the pre-erase bar waveform 34 (as illustrated in FIG. 1B) is shifted to the left of the pre-erase bar waveform 34 such that point E on the pre-erase bar waveform 34 is displayed just to the right of Point D. The post-erase bar waveform 32 and the pre-erase bar waveform 34 combined in the order described above (the pre-erase bar waveform 34 positioned to the right of the post-erase bar waveform 32) together form a scrolling waveform 35. As can be seen in FIG. 1D, Point B, which was the oldest heartbeat data point at time T1, has shifted to the left and as a-result is no longer displayed on the waveform display portion 18. Furthermore, Point H has shifted to the left and is now the oldest heartbeat data point being displayed. Point A, which was the most recent heartbeat data point at time T1, has shifted to the left and is now the second most recent heartbeat data point on the waveform display portion 18. Newly created Point C is now, at time T1+Thb, the most recent heartbeat data point being displayed. As can be seen from the shifting of the heartbeat data points to the left, swapping the positions of the post-erase bar waveform 32 and the pre-erase bar waveform 34 (as displayed by a traditional erase bar display method) after each new heartbeat data point is collected creates a veritable scrolling effect.

The hereinafter described invention uses the above described swapping method to reversibly convert the ECG display unit 10 employing an erase bar waveform display method, as illustrated in FIG. 1A, to an ECG display unit 10 employing a scrolling waveform display method.

FIG. 2A illustrates a block diagram of a circuit 52 connected between an ECG 38 and a display unit 36. The ECG 38 generates a digital video signal 40 containing heartbeat data points in digital form, a vertical sync output signal 44, and a horizontal sync output signal 46. The circuit 52 receives the digital video signal 40, the vertical sync output signal 44, and the horizontal sync output signal 46 and generates a new vertical sync output signal 48 and a transformed digital video data output signal 50. Said transformed digital video data output signal 50 contains the rearranged heartbeat data points in digital form. The display unit 36 receives the new vertical sync output signal 48 and the transformed digital video data output signal 50 as inputs. The display unit 36 displays the scrolling heartbeat data points 42 contained in the transformed digital video data output signal 50. Note, however, that one simply has to remove the circuit 52 from between the display unit 36 and the ECG 38 to restore the erase bar waveform display. Further note that the ECG 38 can be replaced with a similar data producing component.

Figure 2B:
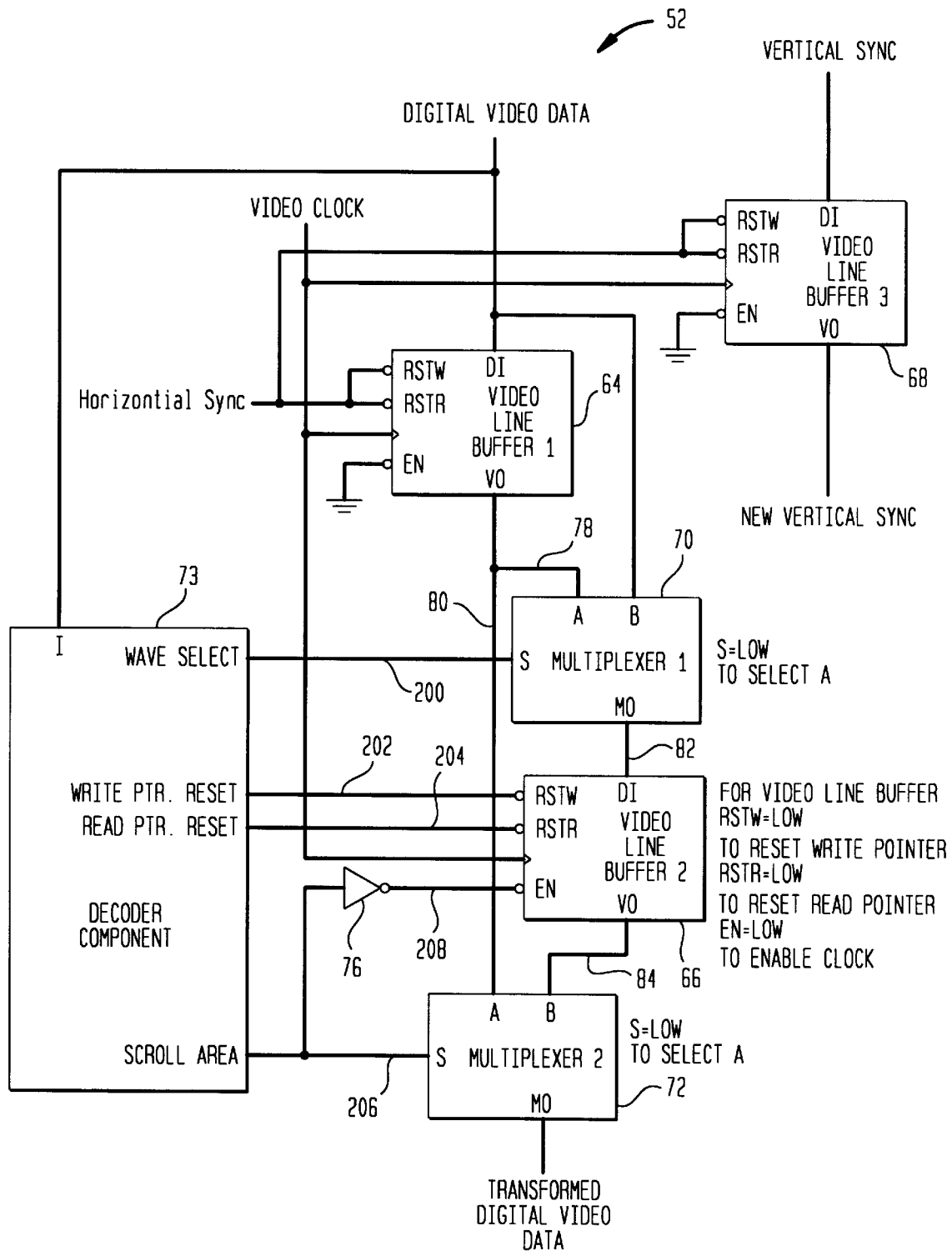
FIG. 2B is a circuit diagram of the invention.

FIG. 2B illustrates a specific embodiment of the circuit 52 as illustrated in FIG. 2A. The circuit 52 consists of a first video line buffer 64, a second video line buffer 66, a third video line buffer 68, a first multiplexor 70, a second multiplexor 72, a decoder component 73, and an inverter 76. The components have the following input and output ports:

The first video line buffer 64, the second video line buffer 66, and the third video line buffer 68 have three common input ports: a write pointer reset input port (labeled RSTW), a read pointer reset input port (labeled RSTR), a data input port (labeled DI), a clock input port (labeled >), and an enable input port (labeled EN). The first video line buffer 64, the second video line buffer 66, and the third video line buffer 68 each have a single output port labeled VO.

The first multiplexor 70 and the second multiplexor 72 each have three input ports: an A input port, a B input port, and a select input port (labeled S). The first multiplexor 70 and the second multiplexor 72 each have an output port labeled MO.

The decoder component 73 has an input port, labeled I, and four output ports labeled Wave Select, Write Ptr. Reset, Read Ptr. Reset, and Scroll Area.

All of the control input ports on each of the video line buffers are active low (the clock is not inverted). All other inputs are active high. The components are connected by the following line connections:

A first input/output line 78 connects the first video line buffer 64 and the first multiplexor 70 between the VO output port and the A input port. A second input/output line 80 connects the first video line buffer 64 and the second multiplexor 72 between the VO output port and the A input port. A third input/output line 82 connects the first multiplexor 70 and the second video line buffer 66 between the MO output port and the DI input port. A fourth input/output line 84 connects the second video line buffer 66 and the second multiplexor 72 between the VO output port and the B input port. A fifth input/output line 200 connects the Wave Select output port of the decoder component 73 and the select input port of the first multiplexor 70. A sixth input/output line 202 connects the Write Ptr. Reset output port of the decoder component 73 to the write pointer reset input port (labeled RSTW) of the second video line buffer 66. A seventh input/output line 204 connects the Read Ptr. Reset output port of the decoder component 73 to the read pointer reset input port (labeled RSTR) of the second video line buffer 66. An eighth input/output line 206 connects the Scroll Area output port of the decoder component 73 to the select input port of the second multiplexor 72. The EN input ports of the first video line buffer 64 and the third video line buffer 68 are connected to ground (always enabled). A ninth input/output line 208 is connected between the EN input port of the second video line buffer 66 and the Scroll Area output port of the decoder component 73. The inverter 76 is connected to the ninth input/output line 208 between the EN input port of the second video line buffer 66 and the Scroll Area output port of the decoder component 73. The components receive the following input signals:

The DI input port of the first video line buffer 64 and the B input port of the first multiplexor 70 receive a Digital Video Data input signal. The DI input port of the third video line buffer 68 receives a Vertical Sync input signal. The write pointer reset input port (labeled RSTW) and the read pointer reset input port (labeled RSTR) of the first video line buffer 64 and of the third video line buffer 68 each receive a Horizontal Sync input signal. The clock input port (labeled >) of each video line buffer receives a common clock input signal, labeled Video Clock.

The purpose of the decoder component 73 is to decode the Digital Video Data input signal. A first portion of this signal contains data indicating the on/off status of the display unit's 36 pixels (see FIG. 2A). A second portion of this signal contains information necessary for the erase bar display to scrolling waveform display transformation. The decoder component 73 decodes the Digital Video Data input signal and generates a Wave Select signal, a Write Ptr. Reset signal, a Read Ptr. Reset signal, and a Scroll Area signal.

The select input port (labeled S) of the first multiplexor 70 receives the Wave Select signal generated by the decoder component 73. The write pointer reset input port (labeled RSTW) of the second video line buffer 66 receives the Write Ptr. Reset signal generated by the decoder component 73. The read pointer reset input port (labeled RSTR) of the second video line buffer 66 receives the Read Ptr. Reset signal, also generated by the decoder component 73. The inverted enable port of the second video line buffer 66 and the select input port (labeled S) of the second multiplexor 72 receive the Scroll Area signal generated by the decoder component 73. The inverted enable port of the second video line buffer 66, however, receives an inverted Scroll Area signal due to the presence of the inverter 76 between the Scroll Area output port of the decoder component 73 and the enable input port of the second video line buffer 66. The circuit 52 generates the following output signals:

The second multiplexor 72 generates a Transformed Digital Video Data output signal which is outputted via the MO output port of the second multiplexor 72. The third video line buffer 68 generates a New Vertical Sync output signal. As most clearly shown in FIG. 2A, the Transformed Digital Video Data output signal and the New Vertical Sync output signal are the final outputs of the entire circuit 52.

Figure 3:
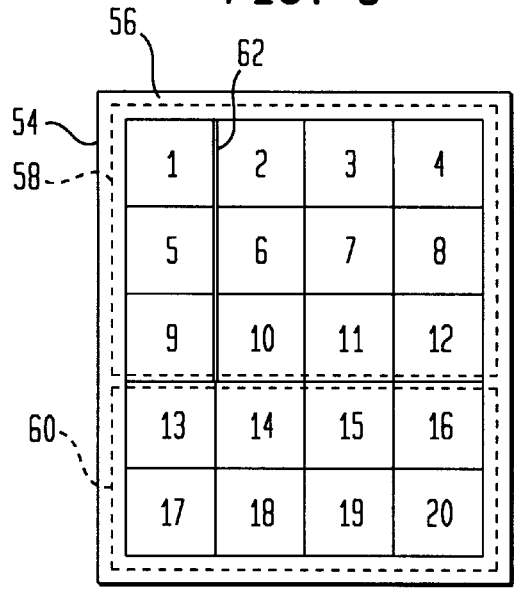
FIG. 3 is a front view of an erase bar waveform display unit screen having 20 pixels with a numeric representation of a data point displayed in each pixel.

The operation of the circuit 52 is best illustrated by first considering a general example. Consider a display unit 54 employing an erase bar waveform display method, as illustrated in FIG. 3. The display unit 54 has a display unit screen 56 that is divided into a 4×5 grid: each rectangle representing a pixel. There are a total of 20 pixels numbered 1–20. Each pixel displays a data point. The data points are numbered 1–20. Pixels 1–12 are dedicated to displaying a waveform and are located within the waveform display portion 58 of the display unit screen 56. Pixels 13–20 are used to display other information such as vital sign numbers and are located within a background portion 60 of the display unit screen 56.

Figure 5:
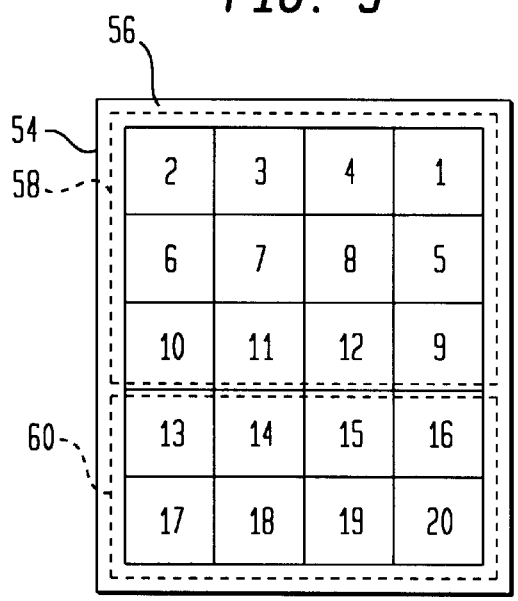
FIG. 5 is a front view of the same display unit screen illustrated in FIG. 4 after the shift down of the data by one line is corrected.

FIG. 3 illustrates the display unit screen 56 frozen at time T and employing an erase bar waveform display method. At time T, an erase bar 62 is between column one and two. For purposes of this illustration, the erase bar 62 has no thickness. In practice, however, the erase bar 62 can have a fixed width of multiple pixels. Data points displayed in pixel 1, 5, and 9, represent the most recent data points displayed. If the circuit 52 is connected to the display unit 54, as illustrated in FIG. 2A, then rather than displaying the display unit screen 56, as illustrated in FIG. 3, the display unit screen 56, as illustrated in FIG. 5, would be displayed. The data points in FIG. 5 are shifted such that the newest data points 1,5, and 9 are displayed in the right most column of pixels (in pixels 4, 8, and 12). Note that the data points in rows 4 and 5, containing data point 13–20, remain in the same position relative to each other in FIG. 5. This is because these data points are displayed by pixels 13–20 which are in the background portion 60 of the display unit screen 56. Only data points displayed by pixels within the waveform display portion 58 of the display unit screen 56 are shifted relative to each other in order to create the scrolling effect. If the circuit 52 is connected, as illustrated in FIG. 2A, the display unit 54 attached to the circuit 52 will not display an erase bar 62. The circuit 52 creates a scrolling waveform by using information which would be displayed on an erase bar waveform display.

Before expanding on the above mentioned example it is very important to have a general understanding of what video line buffers do. Video line buffers basically store inputted data and then output said stored data. As soon as the Write Ptr. Reset signal to the video line buffer is triggered the video line buffer begins to store inputted data. The data points are stored in the video line buffer sequentially, such that the first data point entered is stored in memory location 0 and the second data point entered is stored in memory location 1, etc. As soon as the read pointer reset input signal to the video line buffer is triggered the video line buffer begins to output or "read out" the stored data in a first in first out basis such that the first data point outputted is that stored in memory location 0 and the second data point outputted is that stored in memory location 1, etc.

It is also very important to note that a scanner in a display unit (the piece of equipment which turns each individual pixel on and off) starts at the top of the screen and scans from the left side of the screen to the right side of the screen. The speed by which the scanner scans a row of pixels is predetermined by a user or by the designers of the display unit electronics. The Horizontal Sync input signal and the Vertical Sync input signal received by the circuit 52, as illustrated in FIG. 2A, communicate to the circuit 52 where on the screen and when the scanner is set to begin scanning. This information is important because in order to display data the position of the scanner must be known at all times. The circuit 52 rearranges the order of the Digital Video Data input and then outputs said rearranged data such that the data relating to the on or off status of a pixel is outputted precisely when the scanner passes over said pixel. Therefore, it is extremely important to output data exactly when the scanner is appropriately positioned to display said data.

The goal of circuit 52 is to transform an erase bar display into a scrolling display. As illustrated in FIG. 3, the goal at time T is to shift the data displayed in pixels 2,3 and 4 one pixel to the left and to shift the data displayed in pixel 1 three pixels to the right (and similarly for each row on the screen). Taking into account the operations of the video line buffer and the display unit, as discussed above, data points 2,3,4, and 1, in that order, cannot be displayed in the first row. However, the data points can be displayed, in that order, in the second row. The reason for this constraint is as follows. Without altering the vertical sync of the display unit, the circuit 52 receives data point one at the same time as the scanner passes over pixel 1. At this point in time, the data point displayed in pixel two has not yet been received by the circuit 52 and, therefore, the circuit 52 cannot instruct the scanner to display data point 2 in pixel 1. Only after the scanner reaches the second row can it then display the data points received by the circuit 52 while the scanner was scanning the first row of pixels. As a result of this constraint all of the data points displayed will be shifted one row down. A solution for this down shifting by a row is provided by delaying the vertical sync input signal by a line. This solution will be discussed in further detail after the process of shifting data points is fully explained.

If a display unit has a background portion, such as the one illustrated in FIG. 1A, the data points displayed in each pixel in the background portion 60 must also be shifted one row down. This shifting is necessary because the data points in the waveform display portion 58 of the display unit screen 56 have been shifted down by a row, as discussed above. As long as the data points are displayed in the right positions relative to each other then it does not matter that the entire picture is shifted down by one row because the entire screen can be shifted up by one row, as will be discussed later.

With this background information relating to the operation of video line buffers and display units in mind let us further consider the above mentioned example. Consider FIGS. 2B and 3 side by side. Ignore for now the operation of the third video line buffer 68 illustrated in FIG. 2B. At time T1, the Read Ptr. Reset signal received by the second video line buffer 66 is set low by the decoder component 73 so as to instruct the second line video buffer 66 to start emptying out its stored data points. Since we are at the beginning of the cycle there is no valid stored data to output.

Also at time T1, the Digital Video Data input signal consists of data point 1. Accepting for now the one line down shifting constraint discussed above, data point 1 should be displayed where data point 8 is displayed in FIG. 3. To accomplish this we must wait for the scanner to pass over pixels two through seven before outputting for display data point 1. Data point 1 needs to be delayed the amount of time it takes for the scanner to get to pixel 5 (a one line delay) plus the time the scanner takes to get to pixel 8 (the time it takes to scan all of the pixels in the current row to the right of the erase bar which in this case indicates a three pixel delay). Data point 1 goes through the video line buffer 1 (which creates the one line delay) and then through the first multiplexor 70. The Wave Select signal to the first multiplexor 70 is set low by the decoder component 73 to allow the output of the first video line buffer 64 to pass through the A input port of the first multiplexor 70. The Wave Select signal is set low by the decoder component 73 whenever the data point input would be displayed to the left of the erase bar on an erase bar display. This is the case for data point 1 displayed in pixel 1, as illustrated in FIG. 3. Data point 1 does not pass through the second multiplexor 72 because the Scroll Area signal to the second multiplexor 72 is set high by the decoder component 73. Only data points displayed on pixels that are not within the portion of the display unit screen 56 dedicated to displaying the waveform (such as data points used to display vital sign numbers) pass directly through the second multiplexor 72. These data points pass through the A input port of the second multiplexor 72 after being delayed by one line (this is necessary, as discussed above, to make sure that all of the data points are displayed properly relative to each other). Accordingly, the Scroll Area signal to the second multiplexor 72 is set low by the decoder component 73 whenever the data point entered is not a waveform display data point.

Next, data point 2 enters the circuit 52, i.e. the Digital Video Data input signal consists of data point 2. At the same time, the Write Ptr. Reset signal is set low by the decoder component 73 instructing the second video line buffer 66 to start storing data points. Since data point 2 as displayed in pixel 2 in FIG. 3 is to the right of the erase bar 62, the Wave Select signal to multiplexor 70 is set high by the decoder component 73. As a result, data point 2 does not enter the first video line buffer 64, for a one line delay, rather it passes through the B input port of the first multiplexor 70 and enters the second video line buffer 66. The second video line buffer 66 stores data point 2 in its first memory location, location 0. The purpose of the second video line buffer 66 is to delay the output of data point 2 the amount of time it takes the scanner to scan 3 pixels such that data point 2 is outputted exactly when the scanner is ready to scan pixel 5, as illustrated in FIG. 3.

Next, data point 3 enters the circuit 52, i.e. the Digital Video Data input signal consists of data point 3. Again, since data point 3 is displayed in pixel 3 which is to the right of the erase bar 62 on the erase bar display illustrated in FIG. 3, the Wave Select signal is set high by the decoder component 73 allowing data point 3 to enter the B input port of the first multiplexor 70 and thus pass into the second video line buffer 66. Data point 3 is stored in memory location 1 of the second video line buffer 66.

Next, data point 4 enters the circuit 52, i.e. the Digital Video Data input signal consists of data point 4. Once again, since data point 4 is displayed in pixel 4 which is to the right of the erase bar 62 on the erase bar display illustrated in FIG. 3, the Wave Select signal is set high by the decoder component 73 allowing data point 4 to enter the B input port of the first multiplexor 70 and thus pass into the second video line buffer 66. Data point 4 is stored in memory location 2 of the second video line buffer 66.

Next, data point 1 which was delayed by the first video line buffer 64, by the amount of time it takes the scanner to scan a row, now passes through the A input port of the first multiplexor 70 and enters the second video line buffer 66. The Wave Select signal to the first multiplexor 70 allows data point 1 through the A input port of the first multiplexor 70 because data point 1 would be displayed to the left of the erase bar 62 on the erase bar display. Data point 1 is then stored in memory location 3 of the second video line buffer 66. Data point 1 which has already been delayed by one line by the first video line buffer 64 will be further delayed by three pixels by the second video line buffer 66.

At this point in time, the scanner starts to scan the second row. The Read Ptr. Reset signal to the second video line buffer 66 is set low by the decoder component 73. The Read Ptr. Reset signal is always set low when the scanner begins to start a new row. At this point two things happen simultaneously:

i) data point 2, now stored in memory location 0 of the second video line buffer 66, is displayed in pixel 5; and ii) data point 5 enters the circuit 52.

Figure 4:
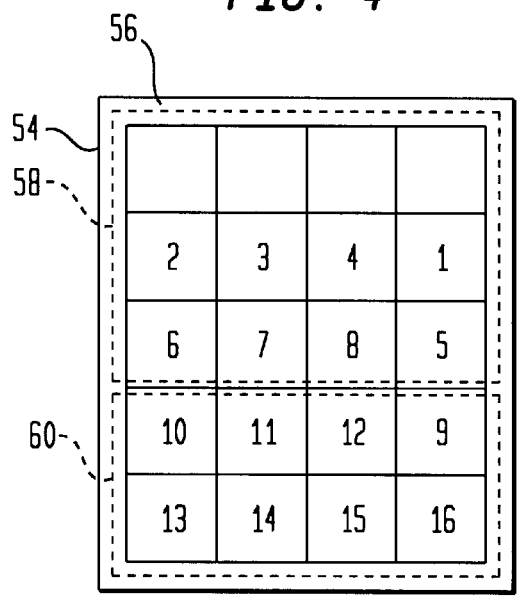
FIG. 4 is a front view of the same display unit screen illustrated in FIG. 3 after the numeric representations of each data point are shifted.

Data point 2 is outputted by the second video line buffer 66, passes through the second multiplexor 72, and is displayed on the display unit screen 56 in pixel 5, as is illustrated in FIG. 4. Data point 5 enters the first video line buffer 64 because it is located to the left of the erase bar on the erase bar waveform display, illustrated in FIG. 3. The first video line buffer 64 delays data point 5 by one line. At this point, the Write Ptr. Reset signal to the second video line buffer 66 is set low by the decoder component 73 to assure that data stored from this point on starts in location 0. The Write Ptr. Reset signal is always set low as soon as the first number in a row to the right of the erase bar enters the circuit 52.

Next, data point 6 enters the circuit 52. At this point in time, just as pixel 5 is about to be scanned, data point 3 which is stored in memory location 1 of the second video line buffer 66 is outputted by the second video line buffer 66, passes through the second multiplexor 72, and is display by pixel 6, as illustrated by FIG. 4. Data point 6 is allowed to pass through the B input port of the first multiplexor 70 because it is located to the right of the erase bar in the erase bar waveform display, and enters the second video line buffer 66. Data point 6 is stored in memory location 0. As data point 6 is being stored the scanner continues its left to right sweep of the second row of pixels and begins to scan pixel 7, as illustrated in FIG. 3.

Next, data point 7 enters the circuit 52. At this point in time, just as pixel 7 is about to be scanned, data point 4, which is stored in memory location 2 of the second video line buffer 66, passes through the second multiplexor 72, and is displayed by pixel 7, as illustrated by FIG. 4. Data point 7 is allowed to pass through the B input port of the first multiplexor 70 because it is located to the right of the erase bar in the erase bar waveform display, and enters the second video line buffer 66. Data point 7 is stored in memory location 1. As data point 7 is being stored the scanner begins to scan pixel 8, as illustrated in FIG. 3.

Next, data point 8 enters the circuit 52. At this point in time, just as pixel 8 is about to be scanned, data point 1, which is stored in memory location 3 of the second video line buffer 66, passes through the second multiplexor 72, and is displayed by pixel 8, as illustrated by FIG. 4. Data point 8 is allowed to pass through the B input port of the first multiplexor 70 (because it is located to the right of the erase bar in the erase bar waveform display) and enters the second video line buffer 66. Data point 8 is stored in memory location 2. As data point 8 is being stored the scanner completes its sweep of the second row of pixels and scans data point 8.

Next, also just before pixel 8 is scanned, data point 5 which was delayed by one line by the first video line buffer 64 passes through the A input port of the first multiplexor 70 and into the second video line buffer 66. The Wave Select signal to the first multiplexor 70 is set low by the decoder component 73, allowing the data point 1 to pass through the A input port of the first multiplexor 70. The Wave Select signal is set low by the decoder component 73 because data point 5 is located to the left of the erase bar 62 in the second row of pixels, as illustrated in FIG. 3. Data point 5 is then stored in memory location 3 of the second video line buffer 66.

Next, the scanner proceeds to the third scan line (the third row of pixels). The same cycle repeats such that:

i)data point 9–12 are stored in the second video line buffer 66 in the following order 10-11-12-9; and ii)data points 5–8 are displayed in the third row, as illustrated in FIG. 4, in the following order: 6-7-8-5.

Next, the scanner proceeds to the fourth scan line. Just before the scanner passes over pixel 13, data point 10 (after being delayed by the 3 pixels) is outputted by the second video line buffer 66, passes through the second multiplexor 72, and is displayed, as illustrated in FIG. 4. Data point 13 enters the circuit 52. The Scroll Area signal to the second multiplexor 72 is set low by the decoder component 73 because data point 13 is not within the waveform display portion 58 of the display unit screen 56 (meaning, that data point 13 is not part of the waveform). As a result, data point 13 enters the first video line buffer 64 and is delayed a full scan line. As the scanner continues to scan, data points 11, 12, and 9, in that order, will be displayed, as illustrated in FIG. 4. Furthermore, data points 14–16 go through the first video line buffer 64 and are also delayed one scan line.

Next, just as the scanner passes over pixel 17 and as data point 17 is entering the circuit 52, data point 13 is outputted by the first video line buffer 64, passes through the second multiplexor 72 and is displayed by pixel 17, as illustrated in FIG. 4. Data point 17 enters the circuit 52, and as data point 13 discussed above, enters the first video line buffer 64 and is delayed a line. As the scanner continues to scan the fifth row, data points 13, 14, 15, and 16, in that order, will be displayed, as illustrated in FIG. 4. Similarly, data points 17–20 enter the first video line buffer 64 and are also delayed one scan line.

As illustrated in FIG. 4, all of the rearranged data has been shifted down by one row and as a result the last row of data has been deleted. This down shifting by a row is the result of the delay imposed on all the data points. In order to adjust for this down shifting the display unit must be instructed to wait a full line (the amount of time it takes to scan an entire row) before displaying any data. This result can be accomplished by delaying the Vertical Sync of the display unit 36, as illustrated in FIG. 2A, by one line. When the Vertical Sync of the display unit (FIG. 2A) is set low by the decoder component 73 (FIG. 2B) the scanner returns to the first row of pixels. Delaying the Vertical Sync signal by one line basically instructs the scanner to start scanning from the top down only as soon as there are data points to be displayed. In the present example case, there are no data points on the first row. Therefore, the Vertical Sync must be delayed by one row. As illustrated in FIG. 2B, this one line delay is accomplished through the use of a third video line buffer 68. The final output display of the circuit 52, as illustrated in FIG. 2B, incorporating a third video line buffer 68, is illustrated in FIG. 5. Notice that only data in the waveform display portion 58 of the display unit screen 56 and not the background portion 60 of the display unit screen 56 has been transformed.

After the next heartbeat data point is displayed the erase bar 62 shifts to the right one column, so that it lies between the second and third pixel columns, and the entire process repeats. The process of rearranging the data points on a frame-by-frame basis and then displaying said rearranged data points creates the desired scrolling effect. As shown above, the Wave Select signal and the Write Ptr. Reset signal are determined by the location of the erase bar 62 (FIG. 3) whereas the Scroll Area signal and the Read Ptr. Reset signal are determined by the location of the waveform area. This allows simple generation of the timing signals by color encoding the Digital Video Data input signal (dedicating a portion of the Digital Video input signal to the on/off status of data points and another portion of the signal to control the operation of the circuit 52 (FIG. 2A and 2A)). Also, since the rearrangement is done on a line-by-line basis controlled by the location of the erase bar 62 (FIG. 3), multiple waveforms can be post-processed to achieve waveforms with different scroll rates.

What is claimed is:

1. A post-processing method for converting an erase bar waveform display to a scrolling waveform display, said erase bar waveform display having a display unit screen, said display unit screen having an erase bar, and a waveform comprising a pre-erase bar portion which is displayed to the left of the erase bar and a post-erase bar portion which is displayed to the right of the erase bar, said pre-erase bar and post-erase bar portions are comprised of data points, said pre-erase bar and post-erase bar portions each have a right most point and a left most point, said post-processing method comprising the steps of: swapping the positions of the pre-erase bar portion and the post-erase bar portion on a frame-by-frame basis such that the right most point of the post-erase bar portion is displayed on the scrolling waveform display just to the left of the left most point of the pre-erase bar portion.

2. The method as claimed in claim 1 wherein the swapping of the pre-erase bar and the post-erase bar portions of the waveform is accomplished by delaying the display of data points in the post-erase bar portion of the waveform on a row-by-row basis by a time period x and by delaying the display of data points in the pre-erase bar portion of the waveform on a row-by-row basis by x plus the amount of time required to scan an entire row of data points, said delays occur on a frame-by-frame basis each time a new data point is ready to be displayed, said time period x is the amount of time required to scan all of the data points displayed in the post-erase bar portion of the waveform on the erase bar waveform display.

3. An apparatus which converts an erase bar waveform display to a scrolling waveform display, said erase bar waveform display having a display unit screen, said display unit screen having an erase bar, a waveform display portion, a waveform displayed within said waveform display portion comprising a pre-erase bar portion which is displayed to the left of the erase bar and a post-erase bar portion which is displayed to the right of the erase bar, said pre-erase bar and post-erase bar portions are comprised of data points, said pre-erase bar and post-erase bar portions each have a right most point and a left most point, said apparatus comprises a circuit which receives data points as inputs and outputs said data points in a different order such that when said reordered data points are displayed on the display unit screen of the scrolling waveform display they form a scrolling waveform.

4. The apparatus as claimed in claim 3 wherein the reordering of the data points is accomplished by swapping the positions of the data points contained in the pre-erase bar portion with the data points contained in the post-erase bar portion on a frame-by-frame basis such that the right most point of the post-erase bar portion is displayed just to the left of the left most point of the pre-erase bar portion.

5. The apparatus as claimed in claim 4 wherein the swapping of the positions of the data points contained in the pre-erase bar and post-erase bar portions is accomplished by delaying the display of data points in the post-erase bar portion of the waveform on a row-by-row basis by a time period x and by delaying the display of data points in the pre-erase bar portion of the waveform on a row-by-row basis by x plus the amount of time required to scan an entire row of data points, said delays occurring on a frame-by-frame basis each time a new data point is ready to be displayed, said time period x is the amount of time required to scan all of the data points displayed in the post-erase bar portion of the waveform on the erase bar waveform display.

6. The apparatus as claimed in claim 5 wherein the circuit comprises a one line delay component and x pixel delay component, the data points displayed in the post-erase bar portion flow through the x pixel delay component and as a result are only outputted by the circuit and thus available to be displayed after a period of time equal to the amount of time it takes a display unit scanner to scan x pixels, data points in the pre-erase bar portion flow through the one line delay component and then through the x pixel delay component and as a result are only outputted by the circuit and thus available for display after a period of time equal to the amount of time it takes for the scanner to scan x pixels plus the amount of time it takes for the scanner to scan a full row of pixels.

7. The apparatus as claimed in claim 6 wherein the circuit further comprises a first switching component which directs all data points that are within a background portion of the erase bar waveform display and that have flown through the one line delay component out of the circuit for display, and a second switching component which directs all data points that form the post-erase bar portion through the x pixel delay component and directs all data points that form the pre-erase bar portion through both the one line delay component and the x pixel delay component.

8. The apparatus as claimed in claim 7 wherein the first switching component has a scroll area select input indicating which data points are displayed within the background portion of the display unit screen; and wherein the second switching component has a wave select input indicating which data points are within the post-erase bar portion and which data points are within the pre-erase bar portion.

9. The apparatus as claimed in claim 8 further comprising a second one line delay component, said second one line delay component accepts as input a vertical sync signal generated by a data producing component which produces the data points to be displayed, said vertical sync signal flows through the second one line delay component and as a result is delayed by the amount of time it takes for the scanner to scan a row of pixels, said one line delay of the vertical sync signal causes the scanner to begin scanning in a top most row of the display unit screen as soon as the first reordered data point is ready to be displayed thereby avoiding a one line down shifting when displaying the data points.

10. The apparatus as claimed in claim 9 wherein the circuit receives an input signal comprising the data points and having encoded within said input signal data needed to control components of said circuit.

* * * * *